United States Patent
Pedersen Fischer

(10) Patent No.: US 10,888,610 B2
(45) Date of Patent: Jan. 12, 2021

(54) IMMUNOGENIC COMPLEX FOR ELICITING PROTECTIVE IMMUNITY AGAINST GROUP B STREPTOCOCCUS

(71) Applicant: MINERVAX APS, Copenhagen N (DK)

(72) Inventor: Per Bo Pedersen Fischer, Frederiksberg (DK)

(73) Assignee: MINERV AX APS

( * ) Notice: Subject to any disclaimer, the term of this patent is extended or adjusted under 35 U.S.C. 154(b) by 0 days.

(21) Appl. No.: 16/067,529

(22) PCT Filed: Dec. 14, 2016

(86) PCT No.: PCT/EP2016/080927
§ 371 (c)(1),
(2) Date: Jun. 29, 2018

(87) PCT Pub. No.: WO2017/114655
PCT Pub. Date: Jul. 6, 2017

(65) Prior Publication Data
US 2019/0282681 A1     Sep. 19, 2019

(30) Foreign Application Priority Data
Dec. 30, 2015 (SE) .................... 1551723

(51) Int. Cl.
*A61K 38/00* (2006.01)
*A61K 39/00* (2006.01)
*A61K 39/02* (2006.01)
*A61K 39/09* (2006.01)
*A61P 37/04* (2006.01)
*A61P 31/04* (2006.01)
*C07K 14/315* (2006.01)

(52) U.S. Cl.
CPC ............ *A61K 39/092* (2013.01); *A61P 31/04* (2018.01); *A61P 37/04* (2018.01); *C07K 14/315* (2013.01); *A61K 2039/55583* (2013.01); *C07K 2319/00* (2013.01)

(58) Field of Classification Search
CPC ........ A61K 38/00; A61K 39/00; A61K 39/02; A61K 39/092
USPC ...... 424/9.1, 9.2, 184.1, 185.1, 234.1, 244.1
See application file for complete search history.

(56) References Cited

FOREIGN PATENT DOCUMENTS

| EP | 0866133 | 3/1998 |
|---|---|---|
| WO | 94/10317 | 5/1994 |
| WO | 94/21685 | 9/1994 |
| WO | 2008/016984 | 2/2008 |
| WO | 2008/127179 | 10/2008 |
| WO | WO2008/127179 | * 10/2008 |

OTHER PUBLICATIONS

Dictionary of Microbiology and Molecular Biology, 2nd edition, eds. Singleton and Sainsbury, Wiley—Interscience publication, John Wiley & sons, New York, p. 452, 1993.*
International Search Report for PCT/EP2016/080927, dated Mar. 7, 2017, 3 pages.
Kong et al., "Molecular Profiles of Group B Streptococcal Surface Protein Antigen Genes: Relationship to Molecular Serotypes", Journal of Clinical Microbiology, Feb. 2002, vol. 40, No. 2, p. 620-626.
Lindahl et al., "Surface Proteins of Streptococcus agalactiae and Related Proteins in Other Bacterial Pathogens", Clinical Microbiology Reviews, Jan. 2005, vol. 18, No. 1, p. 102-127.
Stalhammar-Carlemalm et al., "Nonimmunodominant Regions Are Effective as Building Blocks in a Streptococcal Fusion Protein Vaccine", Cell Host & Microbe 2, 427-434, Dec. 2007.

* cited by examiner

Primary Examiner — Rodney P Swartz
(74) Attorney, Agent, or Firm — Adsero IP

(57) ABSTRACT

The present invention relates to an immunogenic complex comprising an amino acid sequence having at least 80% sequence identity with the amino acid sequence of the N-terminal region of a group B *Streptococcus* surface protein, and a capsular polysaccharide. The immunogenic complex is capable of eliciting protective immunity against group B *Streptococcus*.
The invention further pertains to an immunogenic product comprising the immunogenic complex and an immunogenic fusion protein, the vaccine, the immunogenic complex, or the immunogenic product for use in a method of preventing or treating a group B *Streptococcus* infection, as well as a method of preventing or treating a group B *Streptococcus* infection.

12 Claims, No Drawings
Specification includes a Sequence Listing.

US 10,888,610 B2

IMMUNOGENIC COMPLEX FOR ELICITING PROTECTIVE IMMUNITY AGAINST GROUP B STREPTOCOCCUS

CROSS-REFERENCE TO RELATED APPLICATION

This application claims priority to and is a 35 U.S.C. § 371 national phase application of PCT/EP2016/080927 (WO2017/114655), filed on Dec. 14, 2016 entitled "IMMUNOGENIC COMPLEX FOR ELICITING PROTECTIVE IMMUNITY AGAINST GROUP B STREPTOCOCCUS", which application claims priority to and the benefit of Sweden Patent Application No. 1551723-8, filed Dec. 30, 2015; the disclosures of which are incorporated herein by reference in their entirety.

SEQUENCE STATEMENT

Incorporated by reference herein in its entirety is the Sequence Listing entitled "eolf-seql_0928_19," created Dec. 14, 2016, size of 20 kilobyte.

FIELD OF INVENTION

The present invention relates to the fields of microbiology and vaccine technology, and concerns an immunogenic complex comprising an N-terminal region of a group B Streptococcus surface protein and a capsular polysaccharide. The invention further pertains to an immunogenic product comprising the immunogenic complex and an immunogenic fusion protein, a vaccine comprising the immunogenic complex and/or immunogenic product, and a method of preventing or treating a group B Streptococcus infection.

BACKGROUND OF THE INVENTION

Group B Streptococcus (Streptococcus agalactiae) (GBS) is the major cause of invasive bacterial infections, including meningitis, in the neonatal period. In the United States alone, there are now about 5000 cases per year of invasive disease caused by this bacterium. These infections have an overall mortality of about 10%, and many of the infants that survive have permanent neurological sequelae. In view of this, a large effort has been made to find methods of prevention and treatment and to analyze the mechanisms by which GBS cause infections.

GBS can also cause mastitis in cows, a bovine disease that is of considerable economical importance. Development of a vaccine against GBS infections is therefore of interest also in veterinary medicine.

About 20% of all women are vaginal carriers of GBS, and vertical transmission from the maternal genital tract is probably the most common source of infection in neonatal disease caused by this bacterium. However, only about 1% of the infants that are colonized by the GBS at birth are afflicted by serious infection. Other factors than exposure to the bacterium during birth must therefore contribute to the development of neonatal disease.

Group B streptococcal strains are divided into nine serotypes (Ia, Ib, and II-VIII) based on the structure of the polysaccharide capsule (Baker, J Inf Dis 1990. 161: 917). The four "classical" serotypes Ia, Ib, II, and III occur in roughly equal proportions among strains in the normal flora, but type III is the clinically most important serotype, in particular because it causes most cases of meningitis. Because the capsule is a known virulence factor, it has been studied in considerable detail, in particular in type III strains. Efforts have been made to develop a vaccine, in which the type III polysaccharide capsule would be an essential component.

EP 0 866 133 discloses a vaccine capable of protecting a recipient from infection caused by group B Streptococcus. The invention is directed to the use of a combination of a polysaccharide and a fragment of the epsilon protein. It further discloses that epidemiological data suggest that the type-specific capsule plays an important role in the immunity to group B Streptococcus infections (see page 7 lines 2-3).

The document Gravekamp et al., Infection and Immunity, December 1997, p 5216-5221 discloses the evaluation of the immunogenicity as well as protection of the number of repeats of the alpha (a) C, i.e. AlpC, protein as well as the N-terminal part alone.

WO 9410317 describes the use of the alpha protein, a GBS surface protein, in the development of a conjugate vaccine. A drawback with this protein is that it usually is not expressed by type III strains, which are the cause of many serious GBS infections. Hence, a protective immunity against these strains will not be evoked by an alpha protein vaccine.

WO 9421685 describes the use of the Rib protein, a GBS surface protein, in the development of a vaccine. This protein elicits immunity when administered with alum. However, the Rib protein has the disadvantage that it does not evoke a protective immunity against all GBS strains.

WO 2008127179 describes a fusion protein comprising at least one first N-terminal region fragment of a group B Streptococcus surface protein or analogue, homologue, derivative or immunologically related amino acid sequence or fragments thereof, which is fused to at least one second N-terminal region fragment of a group B Streptococcus surface protein or analogue, homologue, derivative or immunologically related amino acid sequence or fragments thereof, wherein the first and second at least one N-terminal region fragments of group B Streptococcus surface proteins derive from different group B Streptococcus strains, and wherein the fusion protein is capable of eliciting protective immunity against group B Streptococcus.

The document Lindahl et al, Nonimmunodominant Regions Are Effective As Building Blocks In A Streptococcal Fusion Protein Vaccine, Cell Host & Microbe 2, 427-434, December 2007, discloses a fusion protein comprising N-terminal regions of the group B Streptococcus surface proteins Rib and AlpC.

Despite the advances in the progress towards a vaccine suitable for prevention of GBS disease, there is still a need for further methods and vaccines for prevention and treatment of GBS infections. Thus, there remains a need to explore vaccine strategies capable of eliciting protective immunity against a wide range of GBS stains.

Accordingly, it is a primary objective of the present invention to provide an immunogenic complex comprising an N-terminal region of a group B Streptococcus surface protein and a capsular polysaccharide which can be used in a vaccine capable of eliciting protective immunity against GBS infections.

It is a further objective of the present invention to provide a vaccine that elicits protective immunity against many clinically important GBS strains.

Another objective of the present invention is to provide a vaccine comprising a single, or a few, components that elicits protective immunity against GBS infections. A single or a few components has several advantages over a vaccine composed of numerous components, e.g. cost of production and safety.

The means of accomplishing each of the above objectives as well as others will become apparent from the description of the invention which follows hereafter.

SUMMARY OF THE INVENTION

The present invention is based on realization, by the present inventors, that the non-immunodominant N-terminal regions of group B *Streptococcus* surface proteins, of which the use of the N-terminal regions of the surface proteins Rib and AlpC in the form of a fusion protein is disclosed in WO 2008127179, despite their non-immunodominancy can still be useful on their own and not only in the form of a fusion protein. The way to realise this usefulness is to employ these N-terminal regions as carriers for a capsular polysaccharide. As discussed above capsular polysaccharides have been used in vaccines, however, according to EP 0 866 133 the type specific capsule plays a major role in the immunity, thus the width of protection against a range of different group B *Streptococcus* strains is limited using capsular polysaccharides. By using an N-terminal region of a group B *Streptococcus* surface protein as a carrier for the capsular polysaccharide the immunogenicity and scope of protection will be increased.

Thus a first aspect of the present invention relates to an immunogenic complex comprising:
   an amino acid sequence having at least 80% sequence identity with the amino acid sequence of the N-terminal region of a group B *Streptococcus* surface protein, and
   a capsular polysaccharide,
   wherein the immunogenic complex is capable of eliciting protective immunity against group B *Streptococcus*.

A major advantage of the immunogenic complex according to the first aspect of the present invention is that it represents a hybrid between earlier used capsular polysaccharides techniques and the more recent fusion protein techniques to thereby increase the scope of protection obtained. The group B *Streptococcus* surface protein may be selected from surface proteins which are expressed by many clinically important strains of group B *Streptococcus*, and will therefore give the immunogenic complex a wide scope of protection against these important strains. Further the hybrid nature of the immunogenic complex, comprising both an amino acid sequence and a capsular polysaccharide, will provide better immunogenicity than either of the amino acid sequence and the capsular polysaccharide on their own. Thus it is expected that the immunogenic complex will be immunogenic even without adjuvant, although it can also be used with an adjuvant such as alum or Aluminium hydroxide (AlOH).

A second aspect of the present invention pertains to an immunogenic product comprising the immunogenic complex according to the first aspect of the present invention, wherein the immunogenic product further comprises an immunogenic fusion protein comprising:
   a first amino acid sequence having at least 80% sequence identity with the amino acid sequence of the N-terminal region of a first group B *Streptococcus* surface protein, which is fused to
   a second amino acid sequence having at least 80% sequence identity with the amino acid sequence of the N-terminal region of a second group B *Streptococcus* surface protein
   wherein each of the first and the second group B *Streptococcus* surface protein is selected from the group consisting of Rib protein, Alp1 protein, Alp2 protein, Alp3 protein, Alp4 protein and AlpC protein, and wherein the immunogenic fusion protein is capable of eliciting protective immunity against group B *Streptococcus*.

Thus another advantage with the present invention is it also pertains to a immunogenic product which comprises the immunogenic complex according to the first aspect of the present invention combined with an immunogenic fusion protein, such as for example the Rib-AlpC-NN fusion protein of WO 2008127179, thus providing an immunogenic product capable of providing full coverage of protection against all clinically relevant Group B *Streptococcus* strains using only one immunogenic complex and one immunogenic fusion protein.

The third aspect of the present invention pertains to a vaccine comprising a pharmaceutically acceptable vehicle, optionally an adjuvant, and a pharmaceutically effective amount of an immunogenic complex according to the first aspect of the present invention or an immunogenic product according to the second aspect of the present invention, wherein the vaccine is capable of eliciting protective immunity against group B *Streptococcus*.

The corresponding fourth and fifth aspect of the present invention pertain to the immunogenic complex according to the first aspect of the present invention, the immunogenic product according to the second aspect of the present invention, and/or the vaccine according to the third aspect of the present invention for use in a method of preventing or treating an infection caused by a group B *Streptococcus*, and a method of preventing or treating an infection caused by a group B *Streptococcus* comprising administering to the immunogenic complex according to the first aspect of the present invention, the immunogenic product according to the second aspect of the present invention, and/or the vaccine according to the third aspect of the present invention,
respectively.

DETAILED DESCRIPTION OF THE INVENTION

In this specification, unless otherwise specified, "a" or "an" means "one or more".

Throughout the specification, any and all references are specifically incorporated into this patent application by reference.

In a first embodiment of the immunogenic complex according to the first aspect of the present invention the immunogenic complex comprises:
   an amino acid sequence having at least 80% sequence identity with the amino acid sequence of the N-terminal region of a group B *Streptococcus* surface protein, and
   a capsular polysaccharide,
   wherein the immunogenic complex is capable of eliciting protective immunity against group B *Streptococcus*.

The term "immunogenic" is intended to mean having the ability to elicit an immune response. The immunogenic complex of the invention is immunogenic and characterised by its ability to elicit a protective immune response against at least GBS expressing the surface protein of which the N-terminal region is comprised by, or GBS expressing the capsular polysaccharide.

In the complex the amino acid sequence works as a carrier for the capsular polysaccharide. Thus the capsular polysaccharide may be covalently bound to the amino acid sequence The term "sequence identity" indicates a quantitative measure of the degree of homology between two amino acid sequences of equal length or between two nucleotide sequences of equal length. If the two sequences to be compared are not of equal length, they must be aligned to best possible fit. Sequence identity can, for example, be calculated by the BLAST program e.g. the BLASTP program or the BLASTN program (Pearson W. R and D. J. Lipman (1988) PNAS USA 85:2444-2448) (www.ncbl.nlm.nlh.gov/BLAST).

The term "N-terminal region" in relation to the present invention refers to an N-terminus region (N) of a protein. Examples of amino acid sequences of the N-terminal regions of the group B *Streptococcus* surface proteins are given in SEQ IDs NO: 2, 4, 8, 10 and 14.

In particular, examples of N-terminal regions of group B *Streptococcus* proteins include the N-terminal region of the group B *Streptococcus* Rib, Alp1, Alp2, Alp3, Alp4 and AlpC protein, including peptides encoding native amino acid sequences of N-terminal regions of natural Rib, Alp1, Alp2, Alp3, Alp4 and AlpC protein.

Group B Streptococcal strains, also referred herein as GBS, are well known and may be isolated from the blood of infected human beings. GBS is the most common cause of neonatal sepsis in the United States and is responsible for about 5000 cases per year.

The denotation "Group B *streptococcal*" and "Group B *streptococcus*" derives from the fact that *Streptococci* have been divided into immunological groups based upon the presence of specific carbohydrate antigens on their cell surfaces. At present, groups A through 0 are recognized (Davis, B. D. et al., In: Microbiology, 3rd. Edition, page 609, (Harper & Row, 1980).

The capsular polysaccharide is preferably a bacterial polysaccharide, more preferably a group B *Streptococcus* polysaccharide.

The capsular polysaccharide may be serotype specific and selected from group consisting of Group B *Streptococcus* serotypes Ia, Ib, II, III, IV, V, VI, VII, VIII, IX and X.

By polysaccharide is meant any linear or branched polymer consisting of monosaccharide residues, usually linked by glycosidic linkages, and thus includes oligosaccharides. Preferably, the polysaccharide will contain between 2 and 50 monosaccharide unites, more preferably between 6 and 30 monosaccharide units. The polysaccharide component may be based on or derived from polysaccharide components of the polysaccharide capsule from many Gram positive and Gram negative bacterial pathogens such as *H. influenzae, N. meningitidis* and *S. pneumoniae*. Other bacteria from which polysaccharide components may be conjugated to the carrier proteins of the present invention include *Staphylococcus aureus, Klebsiella, Pseudomonas, Salmonella typhi, Pseudomonas 5 aeruginosa*, and *Shigella dysenteriae*. Polysaccharide components suitable for use according to this aspect of the present invention include the Hib oligosaccharide, lipopolysaccharide from *Pseudomonas aeruginosa* (Seid and Sadoff, 1981, "Preparation and characterization of detoxified lipopolysaccharide-protein conjugates. The Journal of Biological Chemistry, Vol. 256, No. 14, Issue of July 25. Pp. 7305-7310), lipopolysaccharides from *Salmonella* (Konadu et al., 1996; "Synthesis, characterization, and immunological properties in mice of conjugates composed of detoxified lipopolysaccharide of *Salmonella* paratyphi a bound to tetanus toxoid with emphasis on the role of 0-acetyls. Infect Immun. Vol. 64, pp. 2709-2715) and the 0-specific polysaccharide from *Shigella dysenteriae* (Chu et al, 1991; "Preparation, characterization, and immunogenicity of conjugates composed of the 0-specific polysaccharide of *Shigella dysenteriae* type 1 (Shig's *bacillus*) bound to tetanus toxoid. Infect Immun., Vol. 59, pp. 4450-4458). Other polysaccharide components suitable for use in accordance with the present invention will be well-known to those skilled in the art. Fragments of bacterial capsular polysaccharide may be produced by any suitable method, such as by acid hydrolysis or ultrasonic irradiation (Szu et al, 1986; "Ultrasonic irradiation of bacterial polysaccharides. Characterization of the depolymerized products and some applications of the process. Carbohydr Res. 1986 September 1, Vol. 152, pp. 7-20). Other methods of preparation of the polysaccharide components will be well known to those of skill in the art.

Preferably, as stated above, the polysaccharide is a capsular polysaccharide derived from group B *Streptococcus*, or their equivalents. The capsular polysaccharide should preferably be coupled to the amino acid sequence by a covalent linkage. A particularly preferred method of coupling polysaccharide and the amino acid sequence is by reductive amination. Other methods include: activation of the polysaccharide with cyanogen bromide followed by reaction with adipic acid dihydrazide (spacer) and by conjugation to carboxide groups of carrier amino acid sequences or protein using soluble carbodiimides (Shneerson et al, 1986; "Quantitative and qualitative analyses of serum antibodies elicited in adults by *Haemophilus influenzae* type b and pneumococcus type 6A capsular polysaccharide-tetanus toxoid conjugates. Infect Immun. 1986 May, Vol. 52(2), pp. 519-528); functionalisation of the carrier amino acid sequence or protein with adipic acid dihydrazide followed by coupling to cyanogen bromide activated polysaccharides (Dick et al, 1989; "Glyconjugates of Bacterial Carbohydrate Antigens: A Survey and Consideration of Design and Preparation Factors. Conjugate Vaccines (Eds. Cruse, et al.)); chemical modification of both the carrier amino acid sequence and the polysaccharide followed by their coupling (Marburg et ad, 1986; "Bimolecular chemistry of macromolecules: synthesis of bacterial polysaccharide conjugates with *Neisseria meningitidis* membrane protein. J. Am. Chem. Soc. 1986, 108, 17, pp. 5282-5287 and Marburg et al, 1987; U.S. Pat. No. 4,695,624 and Marburg et al. 1989, U.S. Pat. No. 4,830, 852).

The polysaccharide molecule may be coupled to the amino acid sequence by a spacer molecule, such as adipic acid. This spacer molecule can be used to facilitate the coupling of amino acid sequence to polysaccharide. After the coupling reaction has been performed, the immunogenic complex or conjugate may be purified by diafiltration or other known methods to remove unreacted amino acid sequence or polysaccharide components.

If the polysaccharide is derived from a bacterial pathogen different from GBS, the conjugate may elicit immunity against two or more pathogens, e.g. multiple types of bacteria. This is a potentially important application of the immunogenic complex.

Multiple capsular polysaccharides may be coupled to the same amino acid sequence. Thus the immunogenic complex may comprise multiple capsular polysaccharides each linked to the amino acid sequence by any of the techniques and/or linkers described above. Where the immunogenic complex comprises multiple capsular polysaccharides the capsular polysaccharides may be identical or different. When the capsular polysaccharides are different they may be derived from different bacteria, e.g. from different Group B *Streptococcus* serotypes.

The number of capsular polysaccharides in the immunogenic complex may thus be one or more such as 1, 2, 3, or more.

The term "protective immunity" in relation to the present invention refers to the ability of serum antibodies and/or cytotoxic T cell response induced during immunization to protect (partially or totally) against disease caused by an infectious agent, such as a group B *Streptococcus*. That is, a vertebrate immunized by the vaccines of the invention will experience limited growth and spread of group B *Streptococcus*. To determine whether protective immunity is induced by a immunogenic complex or vaccine, techniques well known for a person skilled in the art can be used. For example, to determine whether immunization with an immunogenic complex or vaccine according to the invention induces protective immunity against group B *Streptococcus* infection, immunized test animals can be challenged with group B *Streptococcus* and growth and spread of the group B *Streptococcus* is measured.

In the preferred embodiment of the immunogenic complex according to the first aspect of the present invention the group B *Streptococcus* surface protein is selected from the group consisting of Rib protein, Alp1 protein, Alp2 protein, Alp3 protein, Alp4 protein and AlpC protein.

This is advantageous as these proteins are expressed by clinically relevant group B *Streptococcus* serotypes/strains.

The group B *Streptococcus* Rib protein, also referred to in this specification as Rib and Rib protein, is a surface protein known in the art, and for example described in WO 9421685. The denotation "Rib" refers to: Resistance to proteases, immunity, and group B. The Rib protein was first isolated from a group B *streptococcal* strain of serotype III as a distinct 95 kDa protein. Protein Rib is expressed by almost all group B *streptococcal* strains of the clinically important serotype III, which cause most cases of meningitis, and by some strains of other serotypes such as II. Moreover, Rib is expressed by all strains of a hypervirulent clone of type III. A method has been devised to purify protein Rib and it has been demonstrated that antibodies to this protein protect against lethal infection with strains expressing protein Rib (for further details, such as DNA and protein sequences see WO 9421685). The nucleic acid sequence and the amino acid sequence for the N-terminal region of Rib are given in SEQ ID Nos: 1 and 2.

The Alp1 protein is also known as epsilon protein and is a group B *streptococcal* alpha-protein-like protein (Creti et al. *Clin Microbiol.* 2004.42:1326-9).

The nucleic acid sequence and the amino acid sequence for the N-terminal region of Alp1 are given in SEQ ID Nos: 7 and 8.

The Alp2 protein is another alpha-protein-like-protein first identified in a serotype V strain (Lachenauer, C. S., R. Creti, J. L. Michel, and L. C. Madoff. 2000. Mosaicism in the alpha-like protein genes of group B *streptococci*. Proc. Natl. Acad. Sci. USA 97:9630-9635.). Like the other members of the family, the Alp2 protein has an N-terminal domain and several repeated domains towards the C-terminus. Subsequently that protein has been found also in other GBS isolates such as serotypes Ia and III (Lindahl et al. Surface Proteins of *Streptococcus agalactiae* and Related Proteins in Other Bacterial Pathogens, CLINICAL MICROBIOLOGY REVIEWS, January 2005, p. 102-127). The nucleic acid sequence and the amino acid sequence for the N-terminal region of Alp2 are given in SEQ ID Nos: 9 and 10.

The Alp3 protein is yet another alpha-protein-like-protein, also known as R28. It is very similar to the R28 protein also found in *S. pyogenes*. (Lachenauer, C. S., R. Creti, J. L. Michel, and L. C. Madoff. 2000. Mosa icism Mosaicism in the alpha-like protein genes of group B Streptococci. Proc. Natl. Acad. Sci. USA 97:9630-9635 and Lindahl et al. Surface Proteins of *Streptococcus agalactiae* and Related Proteins in Other Bacterial Pathogens, CLINICAL MICROBIOLOGY REVIEWS, January 2005, p. 102-127). The structure is more complex than the other Alpha-protein-like-proteins, but it retains an N-terminal domain which is identical to that of Alp2, and C-terminal repeat regions very similar to Rib. The nucleic acid sequence and the amino acid sequence for the N-terminal region of Alp3 are the same as for Alp2 and are given in SEQ ID Nos: 9 and 10.

The Alp4 protein is an alpha-protein-like-protein so far only identified in the Prague 25/60 strain (Fanrong Kong, Sonia Gowan, Diana Martin, Gregory James, and Gwendolyn L. Gilbert. Molecular Profiles of Group B *Streptococcal* Surface Protein Antigen Genes: Relationship to Molecular Serotypes. JOURNAL OF CLINICAL MICROBIOLOGY, February 2002, p. 620-626). It is a novel member of the Alpha-protein-like family with a structure similar to that of the other members, with a distinct N-terminal domain, and repeat regions towards the C-terminus.

The nucleic acid sequence and the amino acid sequence for the N-terminal region of Alp4 are given in SEQ ID Nos 13 and 14.

The group B *Streptococcus* AlpC protein, also known as alpha protein, is a group B *Streptococcus* surface protein known in the art. WO 9410317 describes a conjugate vaccine composition comprising the alpha protein. The native group B *Streptococcus* AlpC precursor protein as described in WO 9410317 has a molecular weight of 108 kDa. Cleavage of the putative signal sequence of 41 amino acids yields a mature protein of 104 kDa. (Note, however, that the signal sequence was subsequently shown to have a length of 56 amino acid residues: Stålhammar-Carlemalm et al., J Exp Med 177, 1593; 1993). The 20 kDa N-terminal region of the AlpC antigen shows no homology to previously described protein sequences and is followed by a series of nine tandem repeating units that make up 74% of the mature protein. Each repeating unit (denoted herein as "R") is identical and consists of 82 amino acids with a molecular mass of about 8500 Daltons, which is encoded by 246 nucleotides. The C-terminal region of the AlpC antigen contains a cell wall anchor domain motif present in a number of Gram-positive surface proteins.

The nucleic acid sequence and the amino acid sequence for the N-terminal region of AlpC are given in SEQ ID Nos: 3 and 4.

Each of the Rib, Alp1, and AlpC proteins of GBS includes a unique N-terminal region (N) and a long repeat (R) region. The proteins expressed by the GBS strains BM110 and A909 have 12 and 9 repeats, respectively. The wall anchoring regions are located at the C-terminal ends.

The N-terminal regions of Alp2 and Alp3 are identical.

The tandem repeats in Rib and alpha are identical within each protein, but not between the proteins, and vary in number between isolates. Except for this variation, the sequences of Rib and alpha are stable among strains. The two proteins show little or no antigenic cross-reactivity.

More preferably the group B *Streptococcus* surface protein is selected from the group consisting of Alp1 protein, Alp2 protein, Alp3 protein, and Alp4 protein, such as the group consisting of Alp2 protein, Alp3 protein, and Alp4 protein.

In one embodiment of the immunogenic complex according to the first aspect of the present invention the immunogenic complex further comprises a further amino acid sequence having at least 80% sequence identity with the amino acid sequence of the N-terminal region of a further group B *Streptococcus* surface protein This is advantageous as it provides for an immunogenic fusion protein capable of eliciting protective immunity against a larger number of group B *Streptococcus* strains. Thus the further amino acid sequence may be fused to the amino acid sequence to form a fusion protein.

In a further embodiment of the immunogenic complex according to the first aspect of the present invention the further group B *Streptococcus* surface protein is selected from the group consisting of Rib protein, Alp1 protein, Alp2 protein, Alp3 protein, Alp4 protein and AlpC protein.

More preferably the further group B *Streptococcus* surface protein is selected from the group consisting of Alp1 protein, Alp2 protein, Alp3 protein, and Alp4 protein, such as the group consisting of Alp2 protein, Alp3 protein, and Alp4 protein. Where the immunogenic complex comprises multiple capsular polysaccharides each of the capsular polysaccharides may be carried, by being covalently attached or attached via a linker, to a corresponding one of the amino acid sequences. Thus, where the immunogenic complex comprises two capsular polysaccharides and two amino acid sequences one of the capsular polysaccharides may be attached to one of the amino acid sequences and the other of the capsular polysaccharides may attached to the other one of the amino acid sequences.

In one embodiment of the immunogenic complex according to the first aspect of the present invention the group B *Streptococcus* surface protein and the further group B *Streptococcus* surface proteins are derived from different group B *Streptococcus* strains.

This will imply slight variability in the sequence of the N-terminal region fragments but would not alter the biological properties and their functional ability to elicit protective immunity. The group B *Streptococcus* surface protein and the further group B *Streptococcus* surface proteins may also be different. This is advantageous as it increases the number of group B *Streptococcus* strains which the immunogenic complex according to the first aspect of the present invention provides protection against.

In one preferred embodiment of the immunogenic complex according to the first aspect of the present invention there is only one amino acid sequence, having at least 80% sequence identity with the amino acid sequence of the N-terminal region of a group B *Streptococcus* surface protein, in the immunogenic complex.

This means that the immunogenic complex contains only one amino acid sequence having at least 80% sequence identity with the N-terminal region of a group B *Streptococcus* surface protein.

The group B *Streptococcus* surface protein may be selected from the group consisting of Rib protein, Alp1 protein, Alp2 protein, Alp3 protein, Alp4 protein, and AlpC protein.

In a further embodiment of the immunogenic complex according to the first aspect of the present invention the group B *Streptococcus* surface protein and the capsular polysaccharide, and optionally also the further group B *Streptococcus* surface protein, are derived from different group B *Streptococcus* serotypes.

This is advantageous as it increases the number of group B *Streptococcus* serotypes which the immunogenic complex according to the first aspect of the present invention provides protection against.

In a further embodiment of the immunogenic complex according to the first aspect of the present invention the amino acid sequence has at least 80%, such as at least 85%, such as at least 90%, such as 95, 96, 97, 98 or 99% sequence identity with one of the amino acid sequences SEQ IDs 2, 4, 8, 10 and 14, and optionally the further amino acid sequence has at least 80%, such as at least 85%, such as at least 90%, such as 95, 96, 97, 98 or 99% sequence identity with one of the amino acid sequences SEQ IDs 2, 4, 8, 10 and 14.

In the preferred embodiment of the immunogenic complex according to the first aspect of the present invention the amino acid sequence, and optionally also the further amino acid sequence, is conjugated to the capsular polysaccharide. Conjugation encompasses covalently attaching, either directly or via a linker structure or chain as described above. Where the immunogenic complex comprises multiple capsular polysaccharides each capsular polysaccharide may alternatively be conjugated to a single one of the amino acid sequences In one embodiment of the immunogenic complex according to the first aspect of the present invention the amino acid sequence, and optionally also the further amino acid sequence, is modified by glycosylation, amidation, carboxylation or phosphorylation, or by being conjugated to an RSV antigen.

RSV antigens are described below with reference to the third aspect of the present invention.

This is advantageous as such polypeptides, i.e. amino acid sequences, may have enhanced immunogenicity. Such polypeptides may result when the native forms of the polypeptides or fragments thereof are modified or subjected to treatments to enhance their immunogenic character in the intended recipient. Numerous techniques are available and well known to those of skill in the art which may be used, without undue experimentation, to substantially increase the immunogenicity of the polypeptides herein disclosed. For example, the polypeptides may be modified by coupling to dinitrophenol groups or arsanilic acid, or by denaturation with heat and/or SDS. For a review of some general considerations in coupling strategies, see Antibodies, A Laboratory Manual, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

A second aspect of the present invention concerns an immunogenic product comprising the immunogenic complex according to any of the preceding claims, wherein the immunogenic product further comprises and immunogenic fusion protein comprising:

- a first amino acid sequence having at least 80% sequence identity with the amino acid sequence of the N-terminal region of a first group B *Streptococcus* surface protein, which is fused to
- a second amino acid sequence having at least 80% sequence identity with the amino acid sequence of the N-terminal region of a second group B *Streptococcus* surface protein wherein each of the first and the second group B *Streptococcus* surface protein is selected from the group consisting of Rib protein, Alp1 protein, Alp2 protein, Alp3 protein, Alp4 protein and AlpC protein, and wherein the immunogenic fusion protein is capable of eliciting protective immunity against group B *Streptococcus*. This is advantageous as it provides an immunogenic product capable of providing full coverage of protection against all clinically relevant Group B *Streptococcus* strains using only one immunogenic complex and one immunogenic fusion protein.

In the preferred embodiment of the immunogenic product according to the second aspect of the present invention the first amino acid sequence has at least 80%, such as at least 85%, such as at least 90%, such as 95, 96, 97, 98 or 99% sequence identity with one of the amino acid sequences SEQ IDs 2, 4, 8, 10 and 14, and wherein the second amino acid sequence has at least 80%, such as at least 85%, such as at least 90%, such as 95, 96, 97, 98 or 99% sequence identity with one of the amino acid sequences SEQ IDs 2, 4, 8, 10 and 14, or alternatively the immunogenic fusion protein comprises an amino acid sequence having at least 80%, such as at least 85%, such as at least 90%, such as 95, 96, 97, 98 or 99% sequence identity with any one of the amino acid sequences SEQ ID NO:6 and 12.

For the purpose of the present invention the term "fusion protein" refers to an assembly of two or more proteins or or regions of proteins, comprising for example an N-terminal region of a group B *Streptococcus* Alp1 protein and an N-terminal region of a group B *Streptococcus* Alp2 protein. For example there might be one N-terminal region of the Alp1- and one N-terminal region of the Alp2, or 2, 3, 4 or 5 N-terminal region fragments of the Alp1- and the Alp2- proteins, wherein the numbers of N-terminal regions from the two proteins need not be equal.

The combination of polypeptides to provide a fusion protein can be accomplished by coupling or conjugation, either either directly or through an intermediate structure, or by molecular biological fusion, i.e. through the combination of recombinant nucleic acid molecules which comprise fragments of nucleic acid capable of encoding each of the two, such that a single continuous expression product is finally produced.

For the purpose of the present invention the term "protein" refers to a molecular chain of amino acids. A protein is not of a specific length and can, if required, be modified in vivo or in vitro, by, for example, glycosylation, amidation, carboxylation or phosphorylation. Inter alia, amino acid sequences, peptides, oligopeptides and polypeptides are included within the definition. The protein or peptide can be of natural or synthetic origin. In this context a fusion protein is intended to mean two or more polypeptides covalently linked to each other either directly or indirectly by several means such as those mentioned above. The term "fused" means to create a fusion protein as mentioned above.

In addition to, or as replacement for, the immunogenic fusion protein the immunogenic product may comprise one or more further immunogenic complex according to the first aspect of the present invention. Thus the immunogenic product according to the second aspect of the present invention may for example comprise only two immunogenic complexes according to the first aspect of the present invention, only one immunogenic complex and one immunogenic fusion protein as discussed above, two or more immunogenic complexes according to the first aspect of the present invention and one immunogenic fusion protein as discussed above, or two or more immunogenic fusion complexes according to the first aspect of the present invention and two or more immunogenic fusion proteins as discussed above. In each case the amino acid sequence and capsular polysaccharide of the immunogenic complex or complexes may be derived from the same or different serotypes/strains, and the first and second amino acid sequences of the immunogenic fusion protein or fusion proteins may correspond to the N-terminal regions of the same or different group B *Streptococcus* surface proteins. Preferably, in order to obtain a wide scope of protection, each capsular polysaccharide and amino acid sequence, be it in an immunogenic complex or in an immunogenic fusion protein, is derived from different serotypes/strains, and for the amino acid sequences, from different group B *Streptococcus* surface proteins.

Thus one embodiment of the immunogenic product may comprise an immunogenic complex where the group B *Streptococcus* surface protein is Alp1 and where, for the immunogenic fusion protein, the first and the second group B *Streptococcus* surface proteins are Rib and AlpC, respectively.

Another embodiment of the immunogenic product may comprise a first immunogenic complex where the group B *Streptococcus* surface protein is Alp1 or Alp2, a second immunogenic complex where the group B *Streptococcus* surface protein is Rib, and optionally a third immunogenic complex where the group B *Streptococcus* surface protein is AlpC.

In another embodiment of the immunogenic product according to the second aspect of the present invention the group B *Streptococcus* surface protein is selected from the group consisting of Alp1 protein, Alp2 protein, Alp3 protein, and Alp4 protein, and optionally the further group B *Streptococcus* surface protein is selected from the group consisting of Alp1 protein, Alp2 protein, Alp3 protein, and Alp4 protein. The group B *Streptococcus* surface protein and the further group B *Streptococcus* surface protein may be selected from the group consisting of Alp2 protein, Alp3 protein, and Alp4 protein.

In a preferred embodiment of the immunogenic product according to the second aspect of the present invention there is only one amino acid sequence, having at least 80% sequence identity with the amino acid sequence of the N-terminal region of a group B *Streptococcus* surface protein, in the immunogenic complex. This means that the immunogenic complex, in the immunogenic product, contains only a single amino acid sequence having at least 80% sequence identity with the amino acid sequence of the N-terminal region of a group B *Streptococcus* surface protein in the immunogenic complex. The group B *Streptococcus* surface protein may be selected from the group consisting of Rib protein, Alp1 protein, Alp2 protein, Alp3 protein, Alp4 protein, and AlpC protein.

A third aspect of the present invention concerns a vaccine comprising a pharmaceutically acceptable vehicle, optionally an adjuvant, and a pharmaceutically effective amount of an immunogenic complex according to the first aspect of the present invention or an immunogenic product according to the second aspect of the present invention, wherein the vaccine is capable of eliciting protective immunity against group B *Streptococcus*.

The term "pharmaceutical acceptable vehicle" is intended to mean any suitable acceptable excipient, adjuvants, carrier, diluent commonly used in pharmaceutical formulations.

The vaccine may be a vaccine composition.

The vaccine may, in addition to the fusion protein, comprise other pharmacologically acceptable ingredients such as salts, buffers, immunoactive components, adjuvants (AlOH), wetting agents, emulsifying and suspending agents, or sweetening, flavouring, perfuming agents, or other substances which are desirable for improving the efficacy of the composition. A composition is said to be "pharmacologically acceptable" if its administration can be tolerated by a recipient individual.

A multivalent vaccine may also be prepared by combining the immunogenic complex or the immunogenic product with other components, including other fusion proteins as described above, including but not limited to diphtheria toxoid or tetanus toxoid, or polysaccharides, using techniques known in the art. The vaccine may further comprise further antigens such as RSV antigens or *E. coli* antigens. Methods for the preparation and formulation of vaccines and vaccine compositions are well known to those skilled in the art. The choice of ingredients will for instance vary depending on the administration route of the composition. For example compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. In a further embodiment of the third aspect of the present invention the vaccine may comprise an additional immunoactive component. The additional immunoactive component may be an antigen, an immune enhancing substance, and/or a vaccine; either of these may comprise an adjuvant.

Adjuvants are substances that can be used to specifically augment a specific immune response. Normally, the adjuvant and the composition are mixed prior to presentation to the immune system, or presented separately, but into the same site of the animal or human being immunized. Adjuvants can be loosely divided into several groups based upon their composition. These groups include oil adjuvants (for example, Freund's complete and incomplete), mineral salts for example, AlK (SO4)2, AlNa (SO4)2, AlNH4 (SO4), AlOH, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Among those substances particularly useful as adjuvants are saponins such as, for example, Quil A®. Examples of materials suitable for use in vaccine compositions are provided in Remington's Pharmaceutical Sciences (Osol, A, Ed, Mack Publishing Co, Easton, Pa., pp. 1324-1341 (1980).

The vaccine according to the third aspect of the present invention may be administrated parenterally, intramuscularly, intravenously, intraperitoneally, intradermally, mucosally, submucosally, topically or subcutaneously.

The vaccine according to the third aspect may further comprise more than one immunogenic complex according to the first aspect of the present invention. Thus the vaccine may for example comprise a first immunogenic complex where the group B *Streptococcus* surface protein is Alp1 or Alp2, a second immunogenic complex where the group B *Streptococcus* surface protein is Rib, and optionally a third immunogenic complex where the group B *Streptococcus* surface protein is AlpC. The capsular polysaccharides of the first, second, and optionally, third immunogenic complexes may be derived from the same serotype/strain, however it is preferred that the capsular polysaccharides are derived from different serotypes/strains.

Further the vaccine may comprise both an immunogenic complex according to the first aspect of the present invention and an immunogenic product according to the second aspect of the present invention.

The vaccine preferably comprises a pharmaceutically effective amount of an immunogenic product in which the Group B *Streptococcus* surface protein and optionally the further Group B *Streptococcus* surface protein is selected from the group consisting of Alp1 protein, Alp2 protein, Alp3 protein, and Alp4 protein, or in which there is only one amino acid sequence having at least 80% sequence identity with the N-terminal of a Group B *Streptococcus* surface protein.

The group B *Streptococcus* surface protein may be selected from the group consisting of Rib protein, Alp1 protein, Alp2 protein, Alp3 protein, Alp4 protein, and AlpC protein.

Preferable the vaccine comprises aluminium hydroxide as an adjuvant.

Thus, in one embodiment, the vaccine consists of a pharmaceutically effective vehicle, aluminium hydroxide, and an immunogenic product in which there is only one amino acid sequence having at east 80% sequence identity with the N-terminal of a Group B *Streptococcus* surface protein.

The corresponding fourth and fifth aspect of the present invention pertain to the immunogenic complex according to the first aspect of the present invention, the immunogenic product according to the second aspect of the present invention, and/or the vaccine according to the third aspect of the present invention for use in a method of preventing or treating an infection caused by a group B *Streptococcus*, and a method of preventing or treating an infection caused by a group B *Streptococcus* comprising administering to the immunogenic complex according to the first aspect of the present invention, the immunogenic product according to the second aspect of the present invention, and/or the vaccine according to the third aspect of the present invention, respectively.

There is also, according to a further aspect of the present invention, provided a use of the immunogenic complex according to the first aspect of the present invention and/or the immunogenic product according to the second aspect of the present invention for the manufacture of a vaccine for preventing or treating an infection caused by a group B *Streptococcus*.

The immunogenic complex according to the first aspect of the present invention, the immunogenic product according to the second aspect of the present invention, and/or the vaccine according to the third aspect of the present invention may be administered in an effective amount to an individual.

The term "effective amount" in relation to the present invention refers to that amount which provides a therapeutic effect for a given condition and administration regimen. This is a predetermined quantity of active material calculated to produce a desired therapeutic effect in association with the required additives and diluents; i.e., a carrier, or administration vehicle. Further, it is intended to mean an amount sufficient to reduce and most preferably prevent a clinically significant deficit in the activity and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive. Further, the dosage to be administered will vary depending on the active principle or principles to be used, the age, weight etc of the individual to be treated.

The terms "preventing or treating" in its various grammatical forms in relation to the present invention refer to preventing, curing, reversing, attenuating, alleviating, ameliorating, inhibiting, minimizing, suppressing, or halting (1) the deleterious effects of a disorder associated with group B *Streptococcus* infection, (2) disorder progression, or (3) disorder causative agent (group B *Streptococcus*). Further, the terms "preventing or treating" are contemplated to include the creation of total or partial immunity of the individual to group B *Streptococcus* infection.

Maternal immunoprophylaxis with a vaccine, for protecting against infection to group B *Streptococcus* both in the mother and in the young infant, has long been proposed as a potential route.

Thus some embodiments of the corresponding fourth and fifth aspects of the present invention comprise administering to a human female an effective amount of an immunogenic complex, immunogenic product, or vaccine as described herein capable of conferring immunity to the infection to an unborn offspring of the human female.

According to these embodiments, the vaccine is administered to a non-pregnant female or to a pregnant female, under conditions of time and amount sufficient to cause the production of antibodies which serve to protect both the female and a fetus or newborn (via passive transfer of antibodies across the placenta).

A further aspect of the present invention concerns a method for preventing or treating an infection caused by a group B *Streptococcus* which comprises administering to an individual in need thereof an effective amount of antibodies elicited from the exposure of a second individual to an immunogenic complex, immunogenic product and/or a vaccine according to the first, second and/or third aspects of the present invention.

According to this aspect, resistance to group B *Streptococcus* is conferred to the individual by passive immunization, i.e., the immunogenic complex, immunogenic product and/or vaccine is provided to a host (i.e. a human or mammal) volunteer, and the elicited antisera is recovered and directly provided to a recipient suspected of having an infection caused by a group B *Streptococcus*. It is contemplated that such antisera could be administered to a pregnant female (at or prior to parturition), under conditions of time and amount sufficient so that the antisera would serve to protect either the fetus or newborn (via passive incorporation of the antibodies across the placenta).

The vaccine or antisera of the present invention may, thus, be provided either prior to the onset of infection (so as to prevent or attenuate an anticipated infection) or after the initiation of an actual infection.

The vaccine may be administered to humans or animals, including mammals and birds, such as rodents (mouse, rat, guinea pig, or rabbit); birds (turkey, hen or chicken); other farm animals (cow, horse, pig or piglet); pets (dog, cat and other pets); and humans. While many animals may be treated with the vaccine of the invention, a preferred individual for treatment is a human or commercially valuable animal and livestock such as fish, e.g. Tilapia, and camels.

The vaccine can be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, they may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. In this last case the particle size that is used will determine how deep the particles will penetrate into the respiratory tract. Alternatively, application can be via the alimentary route, by combining with the food, feed or drinking water e.g. as a powder, a liquid, or tablet, or by administration directly into the mouth as a: liquid, a gel, a tablet, or a capsule, or to the anus as a suppository. The vaccine may also be administrated in the form of a DNA vaccine.

Many different techniques exist for the timing of the immunizations. It is possible to use the immunogenic complex, immunogenic product and/or vaccine more than once to increase the levels and diversities of expression of the immunoglobulin repertoire expressed by the immunized animal. Typically, if multiple immunizations are given, they will be given one to two months apart.

In the immunogenic product the preferred human dose of the immunogenic fusion protein in the presence of Alhydrogel is within the range of 1 to 250 μg, preferably 10 to 150 μg, preferably 25 to 100 μg or 40 to 80 μg. In the absence of Alhydrogel, the preferred human doses of the immunogenic fusion protein would be 10 to 100 μg, preferably 50 to 500 μg, or preferably 100 to 250 μg.

Generally, the dosage may consist of an initial injection, most probably with adjuvant, followed most probably by one or maybe more booster injections. Preferably, booster injections may be administered at about 1 and 6 months after the initial injection.

The invention claimed is:

1. An immunogenic complex comprising:
   an amino acid sequence having at least 80% sequence identity with the amino acid sequence of the N-terminal region of a group B *Streptococcus* surface protein, and
   a capsular polysaccharide,
   wherein the immunogenic complex is capable of eliciting protective immunity against group B *Streptococcus*,
   wherein the amino acid sequence is conjugated to the capsular polysaccharide, and
   wherein the group B *Streptococcus* surface protein is selected from the group consisting of Rib protein, Alp2 protein, Alp3 protein, Alp4 protein, and AlpC protein, and
   wherein the amino acid sequence has at least 80% sequence identity with one of the amino acid sequences SEQ ID Nos 2, 4, 10 and 14, and
   wherein there is only one amino acid sequence, having at least 80% sequence identity with the amino acid sequence of the N-terminal region of a group B *Streptococcus* surface protein, in the immunogenic complex.

2. The immunogenic complex according to claim 1, wherein the group B *Streptococcus* surface protein is selected from the group consisting of Alp2 protein, Alp3 protein, and Alp4 protein.

3. The immunogenic complex according to claim 1, wherein the group B *Streptococcus* surface protein and the capsular polysaccharide are from different group B *Streptococcus* serotypes.

4. The immunogenic complex according to claim 1, wherein the amino acid sequence is modified by glycosylation, amidation, carboxylation or phosphorylation.

5. An immunogenic complex comprising the
   an amino acid sequence having at least 80% sequence identity with the amino acid sequence of the N-terminal region of a group B *Streptococcus* surface protein, and
   a capsular polysaccharide,
   wherein the immunogenic complex is capable of eliciting protective immunity against group B *Streptococcus*,
   wherein the amino acid sequence is conjugated to the capsular polysaccharide, and
   wherein the group B *Streptococcus* surface protein is selected from the group consisting of Rib protein, Alp1 protein, Alp2 protein, Alp3 protein, Alp4 protein, and AlpC protein, and
   wherein the amino acid sequence has at least 80% sequence identity with one of the amino acid sequences SEQ ID Nos 2, 4, 8, 10 and 14, and
   wherein there is only one amino acid sequence, having at least 80% sequence identity with the amino acid sequence of the N-terminal region of a group B *Streptococcus* surface protein, in the immunogenic complex,
   wherein the immunogenic product further comprises an immunogenic fusion protein comprising:
   a first amino acid sequence having at least 80% sequence identity with the amino acid sequence of the N-terminal region of a first group B *Streptococcus* surface protein, which is fused to
   a second amino acid sequence having at least 80% sequence identity with the amino acid sequence of the N-terminal region of a second group B *Streptococcus* surface protein
   wherein each of the first and the second group B *Streptococcus* surface protein is selected from the group consisting of Rib protein, Alp1 protein, Alp2 protein, Alp3 protein, Alp4 protein and AlpC protein, and
   wherein the immunogenic fusion protein is capable of eliciting protective immunity against group B *Streptococcus*.

6. The immunogenic product according to claim 5, wherein the first amino acid sequence has at least 80% sequence identity with one of the amino acid sequences SEQ ID Nos 2, 4, 8, 10 and 14, and wherein the second amino acid sequence has at least 80% sequence identity with one of the amino acid sequences SEQ ID Nos 2, 4, 8, 10 and 14, or alternatively,
   wherein the immunogenic fusion protein comprises an amino acid sequence having at least 80% sequence identity with any one of the amino acid sequences SEQ ID Nos:6 and 12.

7. The immunogenic product according to claim 5, wherein the group B *Streptococcus* surface protein is selected from the group consisting of Alp1 protein, Alp2 protein, Alp3 protein, and Alp4 protein.

8. A vaccine comprising a pharmaceutically acceptable vehicle and a pharmaceutically effective amount of an immunogenic complex according to claim 1 or an immunogenic product according to claim 5, wherein the vaccine is capable of eliciting protective immunity against group B *Streptococcus*.

9. The vaccine according to claim 8, further comprising aluminium hydroxide as an adjuvant.

10. The vaccine according to claim 9, wherein the vaccine consists of a pharmaceutically effective vehicle, aluminium hydroxide, and the immunogenic product.

11. A method of minimizing or treating an infection caused by a group B *Streptococcus* comprising administering an effective amount of the vaccine according to claim 8 to an individual.

12. The immunogenic product according to claim 7, wherein
    the first group B *Streptococcus* surface protein is Rib, and the second group B *Streptococcus* surface protein is AlpC.

* * * * *

UNITED STATES PATENT AND TRADEMARK OFFICE
CERTIFICATE OF CORRECTION

| | | |
|---|---|---|
| PATENT NO. | : 10,888,610 B2 | Page 1 of 1 |
| APPLICATION NO. | : 16/067529 | |
| DATED | : January 12, 2021 | |
| INVENTOR(S) | : Pedersen Fischer | |

It is certified that error appears in the above-identified patent and that said Letters Patent is hereby corrected as shown below:

On the Title Page

Item (73):
'MINERV AX APS' should read --MINERVAX APS--

In the Claims

At Column 31, Lines 33-34 Claim 5:
'An immunogenic complex comprising the an amino acid sequence having at least 80% sequence' should read --An immunogenic product comprising an amino acid sequence having at least 80% sequence--

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 14

<210> SEQ ID NO 1
<211> LENGTH: 537
<212> TYPE: DNA
<213> ORGANISM: Streptococcus sp.

<400> SEQUENCE: 1
gggcccctgg gatccgctga agtaatttca ggaagtgctg ttacgttaaa cacaaatatg       60
actaaaaatg ttcagaatgg tagagcatat atagatttat atgatgtgaa aaatgggaaa      120
```

```
atagatccat tacaattaat tacgttaaat tcacctgatt taaaagctca gtatgtcatt    180
aggcaaggcg gcaattattt cacacaacct tctgaattga ctactgttgg tgcagctagt    240
attaattata cagtattgaa gacagatgga agtcctcata cgaagcctga tggacaagtg    300
gatattataa acgtttcatt gactatttac aattcttcag ctttgagaga taaaatagat    360
gaagttaaaa agaaagcgga agaccctaaa tgggacgagg aagtcgcgca taaagttttg    420
ataagtttag atgatatcaa aacagatatt gataataatc ctaagacgca atcagacatt    480
gccaataaaa taactgaagt tactaattta gaaaaaatac tagtacctcg aatccca       537
```

<210> SEQ ID NO 2
<211> LENGTH: 179
<212> TYPE: PRT
<213> ORGANISM: Streptococcus sp.

<400> SEQUENCE: 2

```
Gly Pro Leu Gly Ser Ala Glu Val Ile Ser Ser Ala Val Thr Leu
1               5                   10                  15

Asn Thr Asn Met Thr Lys Asn Val Gln Asn Gly Arg Ala Tyr Ile Asp
            20                  25                  30

Leu Tyr Asp Val Lys Asn Gly Lys Ile Asp Pro Leu Gln Leu Ile Thr
        35                  40                  45

Leu Asn Ser Pro Asp Leu Lys Ala Gln Tyr Val Ile Arg Gln Gly Gly
    50                  55                  60

Asn Tyr Phe Thr Gln Pro Ser Glu Leu Thr Thr Val Gly Ala Ala Ser
65                  70                  75                  80

Ile Asn Tyr Thr Val Leu Lys Thr Asp Gly Ser Pro His Thr Lys Pro
                85                  90                  95

Asp Gly Gln Val Asp Ile Ile Asn Val Ser Leu Thr Ile Tyr Asn Ser
            100                 105                 110

Ser Ala Leu Arg Asp Lys Ile Asp Glu Val Lys Lys Lys Ala Glu Asp
        115                 120                 125

Pro Lys Trp Asp Glu Gly Ser Arg Asp Lys Val Leu Ile Ser Leu Asp
    130                 135                 140

Asp Ile Lys Thr Asp Ile Asp Asn Asn Pro Lys Thr Gln Ser Asp Ile
145                 150                 155                 160

Ala Asn Lys Ile Thr Glu Val Thr Asn Leu Glu Lys Ile Leu Val Pro
                165                 170                 175

Arg Ile Pro
```

<210> SEQ ID NO 3
<211> LENGTH: 525
<212> TYPE: DNA
<213> ORGANISM: Streptococcus sp.

<400> SEQUENCE: 3

```
gggcccctgg gatcctctac aattccaggg agtgcagcga ccttaaatac aagcatcact     60
aaaaatatac aaaacggaaa tgcttacata gatttatatg atgtaaaatt aggtaaaata    120
gatccattac aattaattgt tttagaacaa ggttttacag caaagtatgt ttttagacaa    180
ggtactaaat actatgggga tgtttctcag ttgcagagta caggaagggc tagtcttacc    240
tataatatat ttggtgaaga tggactacca catgtaaaga ctgatggaca aattgatata    300
gttagtgttg ctttaactat ttatgattca acaaccttga gggataagat tgaagaagtt    360
agaacgaatg caaacgatcc taagtggacg gaagaaagtc gtactgaggt tttaacagga    420
```

```
ttagatacaa ttaagacaga tattgataat aatcctaaga cgcaaacaga tattgatagt    480
aaaattgttg aggttaatga attagagaaa ttgttagtat tgtca                   525
```

<210> SEQ ID NO 4
<211> LENGTH: 175
<212> TYPE: PRT
<213> ORGANISM: Streptococcus sp.

<400> SEQUENCE: 4

```
Gly Pro Leu Gly Ser Ser Thr Ile Pro Gly Ser Ala Ala Thr Leu Asn
1               5                   10                  15

Thr Ser Ile Thr Lys Asn Ile Gln Asn Gly Asn Ala Tyr Ile Asp Leu
            20                  25                  30

Tyr Asp Val Lys Leu Gly Lys Ile Asp Pro Leu Gln Leu Ile Val Leu
        35                  40                  45

Glu Gln Gly Phe Thr Ala Lys Tyr Val Phe Arg Gln Gly Thr Lys Tyr
    50                  55                  60

Tyr Gly Asp Val Ser Gln Leu Gln Ser Thr Gly Arg Ala Ser Leu Thr
65                  70                  75                  80

Tyr Asn Ile Phe Gly Glu Asp Gly Leu Pro His Val Lys Thr Asp Gly
                85                  90                  95

Gln Ile Asp Ile Val Ser Val Ala Leu Thr Ile Tyr Asp Ser Thr Thr
            100                 105                 110

Leu Arg Asp Lys Ile Glu Glu Val Arg Thr Asn Ala Asn Asp Pro Lys
        115                 120                 125

Trp Thr Glu Glu Ser Arg Thr Glu Val Leu Thr Gly Leu Asp Thr Ile
    130                 135                 140

Lys Thr Asp Ile Asp Asn Asn Pro Lys Thr Gln Thr Asp Ile Asp Ser
145                 150                 155                 160

Lys Ile Val Glu Val Asn Glu Leu Glu Lys Leu Leu Val Leu Ser
                165                 170                 175
```

<210> SEQ ID NO 5
<211> LENGTH: 1053
<212> TYPE: DNA
<213> ORGANISM: Streptococcus sp.

<400> SEQUENCE: 5

```
gggcccctgg gatccgctga agtaatttca ggaagtgctg ttacgttaaa cacaaatatg    60
actaaaaatg ttcagaatgg tagagcatat atagatttat atgatgtgaa aaatgggaaa   120
atagatccat acaattaat tacgttaaat tcacctgatt taaaagctca gtatgtcatt    180
aggcaaggcg gcaattattt cacacaacct tctgaattga ctactgttgg tgcagctagt   240
attaattata cagtattgaa gacagatgga agtcctcata cgaagcctga tggacaagtg   300
gatattataa acgtttcatt gactatttac aattcttcag ctttgagaga taaaatagat   360
gaagttaaaa agaaagcgga agaccctaaa tgggacgagg aagtcgcga taagttttg    420 ataagtttag atgatatcaa aacagatatt gataataatc ctaagacgca atcagacatt   480
gccaataaaa taactgaagt tactaattta gaaaaaatac tagtacctcg aatcccagaa   540
ttctctacaa ttccagggag tgcagcgacc ttaaatacaa gcatcactaa aaatatacaa   600
aacggaaatg cttacataga tttatatgat gtaaaattag gtaaaataga tccattacaa   660
ttaattgttt tagaacaagg ttttacagca agtatgtttt ttagacaagg tactaaatac   720
tatggggatg tttctcagtt gcagagtaca ggaagggcta gtcttaccta atatatattt    780
```

```
ggtgaagatg gactaccaca tgtaaagact gatggacaaa ttgatatagt tagtgttgct    840
ttaactattt atgattcaac aaccttgagg gataagattg aagaagttag aacgaatgca    900
aacgatccta agtggacgga agaaagtcgt actgaggttt taacaggatt agatacaatt    960
aagacagata ttgataataa tcctaagacg caaacagata ttgatagtaa aattgttgag    1020
gttaatgaat tagagaaatt gttagtattg tca                                 1053
```

<210> SEQ ID NO 6
<211> LENGTH: 378
<212> TYPE: PRT
<213> ORGANISM: Streptococcus sp.

<400> SEQUENCE: 6

```
Gly Pro Leu Gly Ser Ala Ser Val Leu Ile Gly Ile Ser Phe Leu Gly
1               5                   10                  15

Gly Phe Thr Gln Gly Gln Phe Asn Ile Ser Thr Asp Thr Val Phe Ala
            20                  25                  30

Ala Glu Val Ile Ser Gly Ser Ala Val Thr Leu Asn Thr Asn Met Thr
        35                  40                  45

Lys Asn Val Gln Asn Gly Arg Ala Tyr Ile Asp Leu Tyr Asp Val Lys
    50                  55                  60

Asn Gly Lys Ile Asp Pro Leu Gln Leu Ile Thr Leu Asn Ser Pro Asp
65                  70                  75                  80

Leu Lys Ala Gln Tyr Val Ile Arg Gln Gly Asn Tyr Phe Thr Gln
                85                  90                  95

Pro Ser Glu Leu Thr Thr Val Gly Ala Ala Ser Ile Asn Tyr Thr Val
            100                 105                 110

Leu Lys Thr Asp Gly Ser Pro His Thr Lys Pro Asp Gly Gln Val Asp
        115                 120                 125

Ile Ile Asn Val Ser Leu Thr Ile Tyr Asn Ser Ser Ala Leu Arg Asp
    130                 135                 140

Lys Ile Asp Glu Val Lys Lys Lys Ala Glu Asp Pro Lys Trp Asp Glu
145                 150                 155                 160

Gly Ser Arg Asp Lys Val Leu Ile Ser Leu Asp Ile Lys Thr Asp
                165                 170                 175

Ile Asp Asn Asn Pro Lys Thr Gln Ser Asp Ile Ala Asn Lys Ile Thr
            180                 185                 190

Glu Val Thr Asn Leu Glu Lys Ile Leu Val Pro Arg Ile Pro Glu Phe
        195                 200                 205

Ser Thr Ile Pro Gly Ser Ala Ala Thr Leu Asn Thr Ser Ile Thr Lys
    210                 215                 220

Asn Ile Gln Asn Gly Asn Ala Tyr Ile Asp Leu Tyr Asp Val Lys Leu
225                 230                 235                 240

Gly Lys Ile Asp Pro Leu Gln Leu Ile Val Leu Glu Gln Gly Phe Thr
                245                 250                 255

Ala Lys Tyr Val Phe Arg Gln Gly Thr Lys Tyr Tyr Gly Asp Val Ser
            260                 265                 270

Gln Leu Gln Ser Thr Gly Arg Ala Ser Leu Thr Tyr Asn Ile Phe Gly
        275                 280                 285

Glu Asp Gly Leu Pro His Val Lys Thr Asp Gly Gln Ile Asp Ile Val
    290                 295                 300

Ser Val Ala Leu Thr Ile Tyr Asp Ser Thr Thr Leu Arg Asp Lys Ile
305                 310                 315                 320
```

Glu Glu Val Arg Thr Asn Ala Asn Asp Pro Lys Trp Thr Glu Ser
            325                 330                 335

Arg Thr Glu Val Leu Thr Gly Leu Asp Thr Ile Lys Thr Asp Ile Asp
        340                 345                 350

Asn Asn Pro Lys Thr Gln Thr Asp Ile Asp Ser Lys Ile Val Glu Val
            355                 360                 365

Asn Glu Leu Glu Lys Leu Leu Val Leu Ser
    370                 375

<210> SEQ ID NO 7
<211> LENGTH: 525
<212> TYPE: DNA
<213> ORGANISM: Streptococcus sp.

<400> SEQUENCE: 7
atggccgaag ttattagcgg tagcgcagca accctgaata gcgcactggt taaaaatgtt      60
agcggtggca aagcctatat cgacatctat gatgtgaaaa acggcaaaat tgatccgctg     120
aatctgattg ttctgcctcc gagcaattat agcgccaact attatatcaa acagggtggt     180 cgcatttca ccaatgttaa tcagctgcag acaccgggta cagcaaccat tacctataac     240
attctggatg aaaatggcaa cccgtatacc aaaagtgatg gccagattga tattgttagc     300
ctggttacca ccgtttatga taccaccgaa ctgcgcaata acatcaacaa agttattgag     360
aatgccaacg acccgaaatg gtcagatgat agccgtaaag atgttctgag caaaatcgag     420
gtgatcaaaa acgatattga taacaacccg aaacccagag cgatatcga caacaaaatt     480 gtggaagtga acgagctgga aaaactgctg gttctgccgt aataa                    525

<210> SEQ ID NO 8
<211> LENGTH: 173
<212> TYPE: PRT
<213> ORGANISM: Streptococcus sp.

<400> SEQUENCE: 8

Met Ala Glu Val Ile Ser Gly Ser Ala Ala Thr Leu Asn Ser Ala Leu
1               5                   10                  15

Val Lys Asn Val Ser Gly Gly Lys Ala Tyr Ile Asp Ile Tyr Asp Val
            20                  25                  30

Lys Asn Gly Lys Ile Asp Pro Leu Asn Leu Ile Val Leu Thr Pro Ser
        35                  40                  45

Asn Tyr Ser Ala Asn Tyr Tyr Ile Lys Gln Gly Gly Arg Ile Phe Thr
    50                  55                  60

Ser Val Asn Gln Leu Gln Thr Pro Gly Thr Ala Thr Ile Thr Tyr Asn
65                  70                  75                  80

Ile Leu Asp Glu Asn Gly Asn Pro Tyr Thr Lys Ser Asp Gly Gln Ile
                85                  90                  95

Asp Ile Val Ser Leu Val Thr Thr Val Tyr Asp Thr Thr Glu Leu Arg
            100                 105                 110

Asn Asn Ile Asn Lys Val Ile Glu Asn Ala Asn Asp Pro Lys Trp Ser
        115                 120                 125

Asp Asp Ser Arg Lys Asp Val Leu Ser Lys Ile Glu Val Ile Lys Asn
    130                 135                 140

Asp Ile Asp Asn Asn Pro Lys Thr Gln Ser Asp Ile Asp Asn Lys Ile
145                 150                 155                 160

Val Glu Val Asn Glu Leu Glu Lys Leu Leu Val Leu Pro
                165                 170

<210> SEQ ID NO 9
<211> LENGTH: 528
<212> TYPE: DNA
<213> ORGANISM: Streptococcus sp.

<400> SEQUENCE: 9

```
atggcaagca ccattccggg tagcgcagca accctgaata ccagcattac caaaaacatt      60
cagaatggca acgcctatat cgatctgtat gatgtgaaaa acggtctgat tgatccgcag     120
aatctgattg ttctgaatcc gagcagctat agcgccaact attatatcaa acagggtgcc     180
aaatattaca gcaacccgag cgaaattacc accaccggta gcgcaaccat tacctttaac     240
attctggatg aaaccggcaa cccgcataaa aaagcagatg gtcagattga tattgtgagc     300
gttaacctga ccatttatga tagcaccgca ctgcgtaatc gtattgatga agttattaac     360
aatgccaacg acccgaaatg gtctgatggt agccgtgatg aagtgctgac cggtctggaa     420
aaaatcaaaa aagatatcga taacaacccg aaacccagat cgacattga caacaaaatt     480
aacgaagtga acgaaatcga aaaactgctg gttgttagcc tgtaataa               528
```

<210> SEQ ID NO 10
<211> LENGTH: 173
<212> TYPE: PRT
<213> ORGANISM: Streptococcus sp.

<400> SEQUENCE: 10

```
Ala Ser Thr Ile Pro Gly Ser Ala Ala Thr Leu Asn Thr Ser Ile Thr
 1               5                  10                  15
Lys Asn Ile Gln Asn Gly Asn Ala Tyr Ile Asp Leu Tyr Asp Val Lys
            20                  25                  30
Asn Gly Leu Ile Asp Pro Gln Asn Leu Ile Val Leu Asn Pro Ser Ser
        35                  40                  45
Tyr Ser Ala Asn Tyr Tyr Ile Lys Gln Gly Ala Lys Tyr Tyr Ser Asn
    50                  55                  60
Pro Ser Glu Ile Thr Thr Thr Gly Ser Ala Thr Ile Thr Phe Asn Ile
65                  70                  75                  80
Leu Asp Glu Thr Gly Asn Pro His Lys Lys Ala Asp Gly Gln Ile Asp
                85                  90                  95
Ile Val Ser Val Asn Leu Thr Ile Tyr Asp Ser Thr Ala Leu Arg Asn
            100                 105                 110
Arg Ile Asp Glu Val Ile Asn Asn Ala Asn Asp Pro Lys Trp Ser Asp
        115                 120                 125
Gly Ser Arg Asp Glu Val Leu Thr Gly Leu Glu Lys Ile Lys Lys Asp
    130                 135                 140
Ile Asp Asn Asn Pro Lys Thr Gln Ile Asp Ile Asp Asn Lys Ile Asn
145                 150                 155                 160
Glu Val Asn Glu Ile Glu Lys Leu Leu Val Val Ser Leu
                165                 170
```

<210> SEQ ID NO 11
<211> LENGTH: 1047
<212> TYPE: DNA
<213> ORGANISM: Streptococcus sp.

<400> SEQUENCE: 11

```
atggccgaag ttattagcgg tagcgcagca accctgaata gcgcactggt taaaaatgtt      60
agcggtggca aagcctatat cgacatctat gatgtgaaaa acggcaaaat tgatccgctg     120
```

```
aatctgattg ttctgcctcc gagcaattat agcgccaact attatatcaa acagggtggt    180
cgcattttca ccaatgttaa tcagctgcag acaccgggta cagcaaccat tacctataac    240
attctggatg aaaatggcaa cccgtatacc aaaagtgatg gccagattga tattgttagc    300
ctggttacca ccgtttatga taccaccgaa ctgcgcaata acatcaacaa agttattgag    360
aatgccaacg acccgaaatg gtcagatgat agccgtaaag atgttctgag caaaatcgag    420
gtgatcaaaa acgatattga taacaacccg aaacccagag cgatatcga caacaaaatt    480 gtggaagtga acgagctgga aaaactgctg gttctgccgg aatttagcac cattccgggt    540
tcagcagcca cactgaatac cagcattacc aaaaacattc agaatggcaa cgcctacatt    600
gatctgtacg atgtaaaaaa tggtctgatc gatccgcaga acctgatcgt gctgaatccg    660
agcagctatt cagccaatta ttatattaaa caaggcgcaa aatactatag caacccgagc    720
gaaattacca ccaccggtag cgccaccatt acgtttaata tcctggacga aaccggtaac    780
ccgcataaaa aagcagatgg tcaaattgat atcgtgagcg ttaacctgac gatttatgat    840
agcacagccc tgcgtaatcg tattgatgaa gtgattaata acgcgaatga tcctaaatgg    900
tccgatggta gtcgtgatga agtactgacc ggtctggaaa aaatcaaaaa agacatcgac    960
aataatccga aacgcagat tgacattgac aataaaatca acgaggtgaa cgagatcgag   1020
aaactgctgg tagttagcct gtaataa                                       1047

<210> SEQ ID NO 12
<211> LENGTH: 347
<212> TYPE: PRT
<213> ORGANISM: Streptococcus sp.

<400> SEQUENCE: 12

Met Ala Glu Val Ile Ser Gly Ser Ala Ala Thr Leu Asn Ser Ala Leu
1               5                   10                  15

Val Lys Asn Val Ser Gly Gly Lys Ala Tyr Ile Asp Ile Tyr Asp Val
            20                  25                  30

Lys Asn Gly Lys Ile Asp Pro Leu Asn Leu Ile Val Leu Thr Pro Ser
        35                  40                  45

Asn Tyr Ser Ala Asn Tyr Tyr Ile Lys Gln Gly Gly Arg Ile Phe Thr
    50                  55                  60

Ser Val Asn Gln Leu Gln Thr Pro Gly Thr Ala Thr Ile Thr Tyr Asn
65                  70                  75                  80

Ile Leu Asp Glu Asn Gly Asn Pro Tyr Thr Lys Ser Asp Gly Gln Ile
                85                  90                  95

Asp Ile Val Ser Leu Val Thr Thr Val Tyr Asp Thr Thr Glu Leu Arg
            100                 105                 110

Asn Asn Ile Asn Lys Val Ile Glu Asn Ala Asn Asp Pro Lys Trp Ser
        115                 120                 125

Asp Asp Ser Arg Lys Asp Val Leu Ser Lys Ile Glu Val Ile Lys Asn
    130                 135                 140

Asp Ile Asp Asn Asn Pro Lys Thr Gln Ser Asp Ile Asp Asn Lys Ile
145                 150                 155                 160

Val Glu Val Asn Glu Leu Glu Lys Leu Leu Val Leu Pro Glu Phe Ser
                165                 170                 175

Thr Ile Pro Gly Ser Ala Ala Thr Leu Asn Thr Ser Ile Thr Lys Asn
            180                 185                 190

Ile Gln Asn Gly Asn Ala Tyr Ile Asp Leu Tyr Asp Val Lys Asn Gly
        195                 200                 205
```

Leu Ile Asp Pro Gln Asn Leu Ile Val Leu Asn Pro Ser Ser Tyr Ser
210                 215                 220

Ala Asn Tyr Tyr Ile Lys Gln Gly Ala Lys Tyr Tyr Ser Asn Pro Ser
225                 230                 235                 240

Glu Ile Thr Thr Thr Gly Ser Ala Thr Ile Thr Phe Asn Ile Leu Asp
            245                 250                 255

Glu Thr Gly Asn Pro His Lys Lys Ala Asp Gly Gln Ile Asp Ile Val
            260                 265                 270

Ser Val Asn Leu Thr Ile Tyr Asp Ser Thr Ala Leu Arg Asn Arg Ile
            275                 280                 285

Asp Glu Val Ile Asn Asn Ala Asn Asp Pro Lys Trp Ser Asp Gly Ser
290                 295                 300

Arg Asp Glu Val Leu Thr Gly Leu Glu Lys Ile Lys Lys Asp Ile Asp
305                 310                 315                 320

Asn Asn Pro Lys Thr Gln Ile Asp Ile Asp Asn Lys Ile Asn Glu Val
                325                 330                 335

Asn Glu Ile Glu Lys Leu Leu Val Val Ser Leu
                340                 345

<210> SEQ ID NO 13
<211> LENGTH: 310
<212> TYPE: DNA
<213> ORGANISM: Streptococcus sp.

<400> SEQUENCE: 13
gtagttgaag gaagtgctgc aacattaaat actgccatga ctaaaaacat gcagaatggg      60
aatgcatata ttgatattta tgatgttaaa ttaggaaaaa ttgatccatt acaactgatt     120
aaattggaac cgggatacac tgctatttat tacattacac aaggttcaaa agtttatgca     180
aatgtttcgg agctacaaac accaggagca gcgaaagtta attatcgtat tcaaacctct     240
gatggaagcg atcatataaa atctgatggt caattagaca gcgttaatat ttcattaaca     300
gtttatgatt                                                            310

<210> SEQ ID NO 14
<211> LENGTH: 103
<212> TYPE: PRT
<213> ORGANISM: Streptococcus sp.

<400> SEQUENCE: 14

Val Val Glu Gly Ser Ala Ala Thr Leu Asn Thr Ala Met Thr Lys Asn
1               5                   10                  15

Met Gln Asn Gly Asn Ala Tyr Ile Asp Ile Tyr Asp Val Lys Leu Gly
            20                  25                  30

Lys Ile Asp Pro Leu Gln Leu Ile Lys Leu Glu Pro Gly Tyr Thr Ala
        35                  40                  45

Ile Tyr Tyr Ile Thr Gln Gly Ser Lys Val Tyr Ala Asn Val Ser Glu
    50                  55                  60

Leu Gln Thr Pro Gly Ala Ala Lys Val Asn Tyr Arg Ile Gln Thr Ser
65                  70                  75                  80

Asp Gly Ser Asp His Ile Lys Ser Asp Gly Gln Leu Asp Ser Val Asn
                85                  90                  95

Ile Ser Leu Thr Val Tyr Asp
            100